(12) United States Patent
Nakamura et al.

(10) Patent No.: US 9,011,545 B2
(45) Date of Patent: Apr. 21, 2015

(54) SPINAL INTERVERTEBRAL DISK REPLACEMENT MATERIAL FOR NUCLEUS PULPOSUS AND PRODUCTION METHOD THEREOF

(71) Applicant: BMG Incorporated, Minami-ku (JP)

(72) Inventors: Takashi Nakamura, Kyoto (JP); Suonghyu Hyon, Uji (JP); Masayuki Kyomoto, Osaka (JP); Makoto Kondo, Osaka (JP)

(73) Assignee: BMG Incorporated, Kyoto (JP)

( * ) Notice: Subject to any disclaimer, the term of this patent is extended or adjusted under 35 U.S.C. 154(b) by 0 days.

(21) Appl. No.: 13/760,739

(22) Filed: Feb. 6, 2013

(65) Prior Publication Data

US 2013/0211527 A1 Aug. 15, 2013

Related U.S. Application Data

(60) Continuation of application No. 12/819,825, filed on Jun. 21, 2010, which is a division of application No. 11/922,119, filed as application No. PCT/JP2006/311641 on Jun. 9, 2006, now abandoned.

(30) Foreign Application Priority Data

Jun. 13, 2005 (JP) ................................. 2005-172672

(51) Int. Cl.
*A61F 2/44* (2006.01)
*A61L 27/16* (2006.01)

(52) U.S. Cl.
CPC *A61F 2/442* (2013.01); *A61L 27/16* (2013.01)

(58) Field of Classification Search
CPC ............................... A61F 2/4611; A61F 2/441
USPC ....................................................... 623/17.16
See application file for complete search history.

(56) References Cited

U.S. PATENT DOCUMENTS

| 4,988,761 A | 1/1991 | Ikada et al. |
| 5,047,055 A | 9/1991 | Bao et al. |

(Continued)

FOREIGN PATENT DOCUMENTS

| EP | 1229873 A2 | 8/2002 |
| JP | 2-086606 A | 3/1990 |

(Continued)

OTHER PUBLICATIONS

Allen et al., "Preclinical Evaluation of Poly (Vinyl Alcohol) Hydrogel Implant as a Replacement for the Nucleus Pulposus", Spine, vol. 29, No. 5, pp. 515-523, (2004).

(Continued)

*Primary Examiner* — Megan McCulley
(74) *Attorney, Agent, or Firm* — Birch, Stewart, Kolasch & Birch, LLP (57) ABSTRACT

The present invention is directed to a method for replacing a nucleus pulposus in an intervertebral disk, which method includes: providing a spinal intervertebral disk replacement molded-dry-product for nucleus pulposus including a polyvinylalcohol gel having a percentage of saturated water content of 18 to 50 wt % before irradiation and being irradiated with γ ray at an intensity of 20 to 100 kGy; and inserting the spinal intervertebral disk replacement molded-dry-product for nucleus pulposus into a prosthetic space inside an anulus fibrosus through an incision opening of the anulus fibrosus, wherein the molded-dry-product changes its shape into an almost cylindrical or almost elliptically cylindrical shape so that a hollow region comes into existence at a shape deformation rate of 150 vol % or more and at a volume swelling ratio of 135 vol % or less by water absorption.

3 Claims, 3 Drawing Sheets

Insertion

Water absorption

(56) References Cited

U.S. PATENT DOCUMENTS

| | | |
|---|---|---|
| 5,192,326 A | 3/1993 | Bao et al. |
| 5,824,903 A | 10/1998 | Nakamura et al. |
| 5,976,186 A | 11/1999 | Bao et al. |
| 6,132,465 A | 10/2000 | Ray et al. |
| 6,224,630 B1 | 5/2001 | Bao et al. |
| 6,264,695 B1 | 7/2001 | Stoy |
| 6,726,721 B2 | 4/2004 | Stoy et al. |
| 7,198,047 B2 | 4/2007 | Lambrecht et al. |
| 2005/0113929 A1 | 5/2005 | Cragg et al. |
| 2005/0187140 A1 | 8/2005 | Hunter et al. |
| 2007/0054990 A1 | 3/2007 | Ruberti et al. |
| 2007/0067039 A1 | 3/2007 | Lambrecbt et al. |

FOREIGN PATENT DOCUMENTS

| | | |
|---|---|---|
| JP | 5-508795 A | 12/1993 |
| JP | 8-098851 A | 4/1996 |
| JP | 10-036534 A | 2/1998 |
| JP | 2003-513685 A | 4/2003 |
| JP | 2005-211353 A | 8/2005 |
| WO | WO 92/10982 A1 | 7/1992 |

OTHER PUBLICATIONS

Full machine translation of JP-10-36534-A, Feb. 10, 1998.

Japanese Office Action dated Jun. 28, 2011 for Application No. 2005-172672.

JPO International Search Report; Appl. No. PCT/JP06/311641; Sep. 12, 2006; pp. 1-2.

Translation of International Preliminary Report on Patentability; Appl. No. PCT/JP06/311641; Mar. 27, 2008, pp. 1-4.

USPTO Advisory Action; U.S. Appl. No. 11/922,119; Jun. 11, 2010, pp. 1-5.

USPTO Applicant Initiated Interview Summary; U.S. Appl. No. 12/819,825; Sep. 25, 2012, pp. 1-3.

USPTO Office Action; U.S. Appl. No. 11/922,119; Feb. 22, 2010; pp. 1-6.

USPTO Office Action; U.S. Appl. No. 11/922,119; Jun. 1, 2009; pp. 1-9.

USPTO Office Action; U.S. Appl. No. 12/819,825; Dec. 7, 2011, pp. 1-10.

USPTO Office Action; U.S. Appl. No. 12/819,825; May 21, 2012, pp. 1-7.

Fig. 1

Insertion    Water absorption

SPINAL INTERVERTEBRAL DISK REPLACEMENT MATERIAL FOR NUCLEUS PULPOSUS AND PRODUCTION METHOD THEREOF

This application is a Continuation of U.S. application Ser. No. 12/819,825 filed on Jun. 21, 2010, which is a division of U.S. application Ser. No. 11/922,119, now abandoned, filed on Apr. 30, 2008 and which is the national phase of PCT International Application No. PCT/JP2006/311641 filed on Jun. 9, 2006. PCT International Application No. PCT/JP2006/311641 claims the benefit of priority of JP 2005-172672, filed on Jun. 13, 2005. The entire contents of each of the above-identified applications are hereby incorporated by reference.

TECHNICAL FIELD

The present invention relates to a spinal intervertebral disk replacement material for nucleus pulposus that is used in the fields such as of orthopedics and neurosurgery, in particular to a spinal intervertebral disk replacement material replacing the nucleus pulposus, the main component of the intervertebral disk, that is used in treatment of the intervertebral disk damaged, for example, by disease such as hernia of intervertebral disk or by accident, and the production method thereof.

BACKGROUND ART

The intervertebral disk is a joint having a function and a structure very complicated functionally and anatomically. It consists of functional structures of anulus fibrosus, vertebral body endplate, and nucleus pulposus. The anulus fibrosus is tough fibrous ring bound to a neighboring vertebral body or a vertebral body endplate. The anulus fibrosus is generally said to have a height of 10 to 15 mm and a thickness of 15 to 20 mm. The nucleus pulposus is placed therein as it is surrounded by the anulus fibrosus. The nucleus pulposus migrates in the anulus fibrosus, when an action such as bending or torsion is applied onto the neighboring vertebral body.

The intervertebral disk may be degraded or damaged by external wound, disease, or aging. In such a case, the nucleus pulposus sticks into the intervertebral foramen, while forming hernia. The nucleus pulposus sticking out pressurizes the spinal cord, causing pain and paralysis of the neighboring structures or pain and paralysis of the lower limbs. Alternatively, it is calcified by aging, becoming less compatible with water and gradually contracted. The nucleus pulposus then cannot retain its favorable interbody distance any more, and cause damage of the upper or lower vertebral body.

Currently, patients with a disease related to the intervertebral disk that plays an important role in the body, such as hernia of intervertebral disk, are treated by interbody fixation by using, for example, an autotransplantation bone, bone cement or synthetic vertebral body spacer after extraction of the affected intervertebral disk. However, these therapies are aimed at fixation of the vertebral body, and the mechanical properties inherent to the intervertebral disk such as flexibility and load-buffering action are neglected. As a result, such a therapy exerts an adverse effect on the neighboring upper and lower vertebral bodies, causing secondary damages of the intervertebral disks.

On the other hand, the hernia of intervertebral disk is known to be induced for example by aging of the nucleus pulposus. In the case of a relatively milder disorder, a therapy of replacing only the aged nucleus pulposus is more desirable than the vertebral body fusion. Thus, it is preferable to perform local or entire replacement by using a synthetic prosthesis having a function to assure sufficient mobility of the intervertebral disk, while mimicking the natural physiological function of the intervertebral disk and preserving the normal interbody space. they also had some problems. These prostheses are large implants demanding partial removal of the neighboring upper and lower vertebral bodies and entire replacement of the intervertebral disk and the neighboring structures, and thus, had a possibility of imposing a very high load on the patient during operation. In addition, such a device was higher in rigidity and thus, undesirable from the point of material mechanics.

Accordingly, these prostheses smaller in size were developed. Such a smaller prosthesis is intended to be used for replacement only of the nucleus pulposus in the intervertebral disk. For example Bao Qi-Bin et al. studied replacement of the body nucleus pulposus with a hydrogel (see Patent Documents 1, 2, and 3). Alternatively, Charles D. Ray et al. also prepared a prosthesis in combination of polyethylene and a hydrogel aimed at replacement of the body nucleus pulposus (see Patent Documents 4 and 5). PVA hydrogels, which have favorable repeated load resistance and shock-relaxing property even under repeated pump action of absorbing and releasing structural water into and out of the hydrogel, are favorable as the materials for synthetic nucleus pulposus prosthesis.

Such a synthetic nucleus pulposus prosthesis is inserted into the space between the anulus fibrosus and a vertebral body cartilage called vertebral body endplate at the affected intervertebral disk site. The inserted synthetic nucleus pulposus prosthesis in the body anulus fibrosus is considered to move vigorously vertically and horizontally occasionally under a load of several times larger than the body weight.

The synthetic nucleus pulposus prosthesis may possibly be separated from the anulus fibrosus under a load of varying magnitude. If it is separated, the intervertebral disk that had the separated synthetic nucleus pulposus prosthesis may not have sufficient load resistance and damage the intervertebral disk and the neighboring upper and lower vertebral bodies. In addition, the implant itself has a possibility of damaging the neighboring structures and nerves. Thus, it is quite important to prevent separation of the synthetic nucleus pulposus prosthesis after operation.

In replacement of the body nucleus pulposus with a synthetic nucleus pulposus prosthesis, it was necessary to form an opening in the anulus fibrosus and an insertion route thereto. If a synthetic nucleus pulposus prosthesis is separated, it would be separated from the opening and the insertion route thus formed. Reduction in size of the opening and the insertion route leads to fewer frequency of the separation of synthetic nucleus pulposus prosthesis. In addition, it also leads to reduction of the damage on anulus fibrosus and thus, to decrease in the possibility of complications induced. Further, if the replaced synthetic nucleus pulposus prosthesis, after insertion, happens to become larger than the opening and the insertion route formed in the anulus fibrosus by some denaturation or deformation, it would not be separated in principle from the opening or the insertion route.

For that reason, Bao et al. disclosed a prosthesis prepared with a hydrogel in the study described above, which was inserted into the anulus fibrosus in the dehydrated state and expanded therein by hydration. The study by Bao et al. and other similar studies depended only on hydration of the hydrogel and demanded a very high water content of about 55 to 99% for desirable expansion. As a result, the resulting prosthesis is lower in load resistance, possibly causing recurrence of the hernia condition by deformation under application of high load. In addition, reconstruction of the structure is dependent on the condition of the surrounding anulus fibrosus. Thus, incomplete condition of the anulus fibrosus may result in separation of the prosthesis without functioning as the intervertebral disk. In addition, a prosthesis with insufficient load resistance demands an instrument for fixing the vertebral body for compensation of low load resistance, which may lead to increase of the load on the patient. Swelling of the hydrogel is restricted only by the body anulus fibrosus. The essentially uncontrolled swelling may raise a concern about recurrence of the hernia condition. In addition, it may prevent healing of, or even worsen, the anulus fibrosus opening that was cut open for insertion. Actually in an animal test by using baboons, there were 6 cases of separation in the 20 cases tested. Further in some of them, the separation occurred from the sites other than the inserted anulus fibrosus opening site, indicating that the load resistance was insufficient (see Non-patent Literature 1).

Ray et al. also studied a prosthesis of hydrogel system, which was also inserted into the anulus fibrosus in the dehydrated state. In the prosthesis, expansion of the hydrogel was restricted as it is covered with a polymeric woven-fabric jacket such as of polyethylene on the periphery. However, because the polymeric woven-fabric jacket used was relatively rigid and almost resistant to shrinkage, swelling, denaturation, or deformation, the prosthesis had a problem that it was larger also in the dry state. Thus, improvement was made to insert two prostheses that were significantly smaller in size than the anulus fibrosus lumen. In the method of inserting two prostheses, a small incision opening is formed in the anulus fibrosus and the prostheses are inserted one by one. This prosthesis-inserting method is advantageous in that the incision opening of the anulus fibrosus is smaller, but the shape of the substantially smaller prosthesis and that of the anulus-fibrosus incision opening are almost the same, and under application of a mechanical force such as bending or torsion, the individual prostheses may be separated out of the anulus fibrosus one by one. To solve the problems above, the two prostheses are bound to each other with a string. It solved some of the problems associated with separation. However, because the core hydrogel has a high water content, the prosthesis also raises a concern about its low load resistance. During movement of the prosthesis in anulus fibrosus, the relatively rigid polymeric woven-fabric jacket may damage the upper and lower vertebral body cartilages significantly and thus, such a prosthesis is not favorable as a prosthesis for replacement of nucleus pulposus surrounded by the endplate cartilage and the anulus fibrosus. Further, the two prostheses inserted into the anulus fibrosus raises concerns about abrasion between them, generation of unexpected abrasion powder, and breakage of the polymer woven fabric jacket.

Currently in the rapidly graying society, diseases caused by the intervertebral disk denatured or damaged by aging, external wound, or disease are significant threat to patients. Thus, proper recovery of the function of the damaged intervertebral disk is important.

However, because the synthetic nucleus pulposus prosthesis described above has a practical water content of approximately 55 to 99 wt %, it raised a concern about low load resistance and recurrence of the hernia condition by deformation under application of high load. Further, reconstruction of the structure is dependent on the condition of the surrounding anulus fibrosus. Thus, incomplete condition of the anulus fibrosus may result in separation of the prosthesis from anulus fibrosus without functioning as the intervertebral disk and possible occurrence of damage caused thereby. In addition, a prosthesis with insufficient load resistance demands an instrument for fixing the vertebral body for compensation of low load resistance, which may lead to increase of the load on the patient. Further, abrasion with the neighboring vertebral body cartilage endplates may also cause damage of the peripheral structures.

Bao et al. reported a method of inserting at least one hydrophilic xerogel rod into the cavity of anulus fibrosus having no the natural nucleus and completely filling the cavity by expansion of the hydrogel by water absorption (Patent Document 6). However, it was not possible to control the shape of the hydrophilic xerogel rod in anulus fibrosus, and disadvantageously, the densely filled site raised a concern about recurrence of hernia, while the coarsely filled site raised a concern about insufficient load resistance. It also caused a concern about generation of unexpected abrasion powder by abrasion among xerogel rods inserted and bent in the anulus fibrosus.

Patent Document 1: U.S. Pat. No. 5,047,055
Patent Document 2: U.S. Pat. No. 5,192,326
Patent Document 3: U.S. Pat. No. 5,976,186
Patent Document 4: U.S. Pat. No. 5,824,903
Patent Document 5: U.S. Pat. No. 6,132,465
Patent Document 6: Japanese Unexamined Patent Publication No. 8-98851
Non-patent Literature 1: "Preclinical Evaluation of a Poly (Vinyl Alcohol) Hydrogel Implant as a Replacement for the Nucleus Pulposus", SPINE, VOL. 29, NO. 5, 2004

DISCLOSURE OF INVENTION

Technical Problems to be Solved

An object of the present invention, which was made to solve the problems above, is to provide a spinal intervertebral disk replacement material for nucleus pulposus which is relatively superior in load resistance that causes smaller damage of the anulus fibrosus by insertion during operation, remains in the anulus fibrosus stably after operation, and also allows prevention of the damage of the vertebral body cartilage endplate and the anulus fibrosus surrounding the prosthetic portion by sliding.

Means to Solve the Problems

The present invention relates to a spinal intervertebral disk replacement material for nucleus pulposus, comprising a dry polyvinylalcohol gel having a percentage of saturated water content of 18 to 50 wt % that changes its shape at a shape deformation rate of 150 vol % or more by water absorption.

The present invention also relates to a method of producing the spinal intervertebral disk replacement material for nucleus pulposus above, comprising a step of preparing a polyvinylalcohol gel having a percentage of saturated water content of 20 to 53 wt %, a step of converting the polyvinylalcohol gel into a polyvinylalcohol hydrogel in the hydrated state and forming it into a shape having a hollow region, a step of irradiating the polyvinylalcohol hydrogel with γ ray at an intensity of 20 to 100 kGy, and a step of drying the PVA hydrogel in such a manner that the resulting hydrogel is so deformed that the hollow region disappears.

Effects of the Invention

In the present invention, the spinal intervertebral disk replacement material is obtained as a material in the rod shape by processing a replacement material of polyvinylalcohol into a shape returning (deforming itself) to the shape of the nucleus pulposus to be replaced so that the replacement material can be inserted in the dehydrated state through the incision opening for insertion into the prosthetic space, and it is inserted as it is into the prosthetic space. Then, the spinal intervertebral disk replacement material deforms itself by absorption of body fluid, occupying the entire prosthetic space. It is thus possible to prevent damage of the insertion site (e.g., anulus fibrosus) during operation, without concern about separation of migration.

It is also possible to raise the load resistance and eliminate the concern about breakage, excessive deformation, separation, and others under application of load, by controlling the percentage of saturated water content after water absorption in a particular range. It is thus possible to reduce the load to the patient, without need for an additional instrument for fixing the vertebral body. It is also possible to prevent the damage of the vertebral body cartilage endplate and the anulus fibrosus surrounding the prosthetic portion.

In addition, the replacement material according to the present invention remembers the shape after water absorption and allows control of the shape in the prosthetic space, and thus, there is no unexpected highly or scarcely filled site formed in the prosthetic space. Further, there is no abrasion powder generated by abrasion among the replacement materials.

EXPLANATION OF NUMERALS

1: Anulus fibrosus,
2: Space when nucleus pulposus is removed,
3: Incision opening formed for insertion of spinal intervertebral disk replacement material,
4: Spinal intervertebral disk replacement material,
4a: Hollow region, and
5: Slit.

BEST MODE FOR CARRYING OUT THE INVENTION

Figure 1:
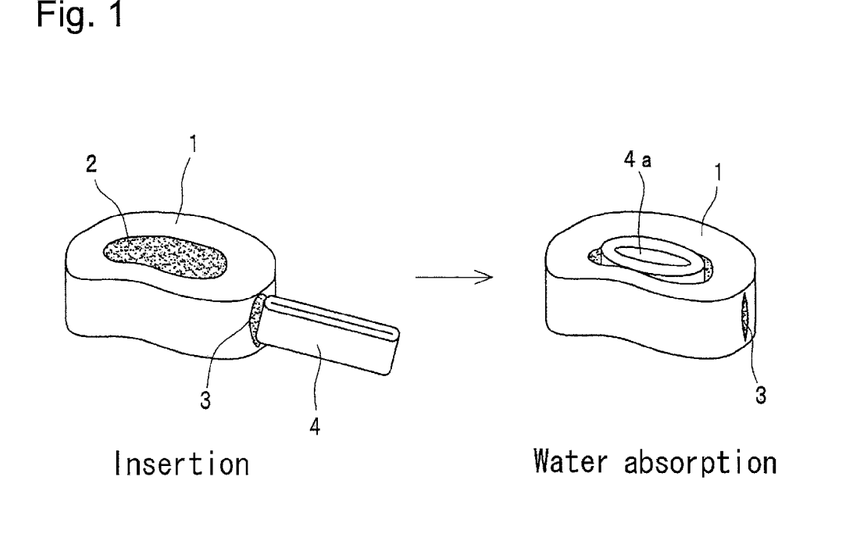
FIG. 1 is a schematic explanatory view illustrating the use example of a spinal intervertebral disk replacement material according to the present invention.

Use Example of Spinal Intervertebral Disk Replacement Material for Nucleus Pulposus An example of use of the spinal intervertebral disk replacement material for nucleus pulposus according to the present invention (hereinafter, referred to simply as replacement material) will be described briefly with reference to FIG. 1. FIG. 1 is a schematic explanatory view illustrating an example of the replacement material according to the present invention that becomes in a hollow-disk shape (almost cylindrical or almost elliptically cylindrical) by water absorption.

In FIG. 1, the numeral 1 represents the anulus fibrosus surrounding nucleus pulposus, 2 represents prosthetic space (e.g., space where the nucleus pulposus is removed), 3 represents the incision opening formed for insertion of the replacement material according to the present invention, and 4 represents the replacement material according to the present invention. The replacement material 4 deforms itself by water absorption into the shape fitted to the prosthetic space 2, as will be described in detail later. The replacement material 4 after water absorption has a hollow disk shape (almost cylindrical or almost elliptically cylindrical) having a hollow region 4a, but has a rod-shaped shape with deformed hollow region 4a in the dehydrated condition before insertion. Thus, it is possible to insert the replacement material 4 into the prosthetic space 2 through the incision opening 3. After insertion, the replacement material 4 is moistened with the body fluid into the hydrated state, occupying the prosthetic space 2. Thus, there is no concern about drop or separation of the replacement material.

(Spinal Intervertebral Disk Replacement Material for Nucleus Pulposus)

The spinal intervertebral disk replacement material for nucleus pulposus according to the present invention is a material replacing nucleus pulposus that is made of a dry polyvinylalcohol gel having a percentage of saturated water content of 18 to 50 wt %, preferably 23 to 35 wt % and changes its shape by water absorption.

The dry polyvinylalcohol gel according to the present invention for the replacement material is a dry polyvinylalcohol gel crosslinked three-dimensionally that swells at the percentage of saturated water content. On the other hand, the polyvinylalcohol hydrogel means jelly polyvinylalcohol formed after water absorption.

Hereinafter, polyvinylalcohol will be referred to simply as PVA.

It is possible to make the replacement material withstand sufficient load, by adjusting the percentage of saturated water content of the dry PVA gel for the replacement material according to the present invention in the range above. With sufficient load resistance, the replacement material can withstand a load generated in everyday life and several times larger than the body weight as it is. Accordingly, it is possible to reduce the concerns about breakage, excessive deformation, separation, and others when load is applied. There is also no need for an additional instrument for fixing the vertebral body, and thus, it is possible to reduce the load on the patient. In addition, in the favorable range of water content above, it is possible to prevent damage on the vertebral body cartilage endplate and the anulus fibrosus in the area surrounding the prosthetic portion.

When the water content is too small, the pump action of the PVA hydrogel of releasing internal water and absorbing external water is not in operation in the prosthetic area, and thus, sufficient repeated load resistance and shock-relaxing property are not performed. In addition, low water content leads to high PVA hydrogel rigidity, possibly damaging the vertebral body cartilage endplate and the anulus fibrosus surrounding the prosthetic portion. It is also extremely difficult and disadvantageous industrially to prepare a uniform dry PVA gel having an excessively small percentage of saturated water content.

When the water content is too large, it is difficult to satisfy the requirements in mechanical properties of human intervertebral disk such as compression rigidity, axial Young's modulus, torsional rigidity, and torsional Young's modulus, and thus, to make it have the function inherent to the intervertebral disk. For example, insufficient load resistance is performed, and there is possibility of breakage, excessive deformation, separation and other under application of load. Alternatively, excessively large percentage of saturated water content leads to drastic decrease in PVA crosslinking efficiency by γ-ray irradiation, and the resulting prosthetic material becomes less variable in shape.

In the invention, the percentage of saturated water content is determined in the following manner: A test specimen is dried at a reduced pressure of 1 Torr under vacuum at 40 to 60° C. for 48 hours or more, and the dry weight ($W_1$) thereof is determined. After measurement of the dry weight, the test specimen is immersed in hot water at 40° C. for 48 hours or more. After saturation of the sample water content, the test specimen is transferred rapidly into a weighing bottle and sealed therein with a cap, and the wet weight ($W_2$) thereof is determined. The water content is calculated according to the following Formula.

Water content (wt %)=$(W_2-W_1) \times 100/W_1$

The rate of the shape deformation when the replacement material according to the present invention changes its shape by water absorption is 150 vol % or more, preferably 160 vol % or more, and more preferably 200 vol % or more. An excessively small shape deformation rate may lead to insufficient occupation of the prosthetic space, which in turn leads to drop or separation of the replacement material out of the anulus fibrosus, when it is exposed to mechanical action such as bending or torsion. Alternatively, the replacement material may not be sufficiently reduced in size even in the dehydrated state, and thus, it is difficult to prevent damage into the insertion site effectively during operation.

The shape deformation rate is the ratio of the apparent volume in the hydrated state to the apparent volume in the dehydrated state (hydration state/dehydration state). The apparent volume is the volume totaling not only a volume of the replacement material itself but also a volume of the hollow region formed by deformation, which is determined by measuring the composite of the replacement material with a packing material, such as silicon rubber, packed in the hollow region.

In the present description, the volume is determined by the Archimedes' method. In particular, the volume of the replacement material in the dehydrated state should be determined in a very short period of time before the replacement material is hydrated.

In measurement of the volume in the dehydrated state, a replacement material previously dried under a reduced pressure at 1 Torr at room temperature for 48 hours is used. Alternatively in measurement of the volume in the hydrated state, at 37° C., a replacement material previously immersed in physiological saline for 24 hours is used.

The change in shape of the replacement material according to the present invention caused by water absorption is based on the ability of shape memory of the replacement material. The ability of shape memory, as used here in the present invention, means that a dry polyvinylalcohol gel for replacement material potentially has a particular wet shape, and has the wet shape when it is shifted from the dehydrated state into the hydrated state. Thus, the replacement material according to the present invention has memory of the shape in the wet state and reclaims its shape when it is shifted from the dehydrated state into the hydrated state. The replacement material according to the present invention, which has such an ability of shape memory, can change its shape by water absorption.

The replacement material according to the present invention changes its shape in such a manner that it has a hollow region newly formed by water absorption. Because the replacement material according to the present invention can have a shape with the hollow region disappeared, for example a shape with the hollow region flattened, in the dehydrated state, it is possible to reduce the size of the replacement material in the dehydrated state. As a result, it is possible to prevent damage of the insertion site (e.g., anulus fibrosus) during operation. When the replacement material does not expose the hollow region by water absorption, the replacement material is rigid at the center even in the hydrated state, cannot contract in size in the dehydrated state, and as a result, damages the insertion site (e.g., anulus fibrosus) significantly during operation. If the replacement material is made rod-shaped for prevention of the damage at the insertion site during insertion, the change in shape by water absorption is not sufficient and thus, there still remains an unresolved concern about migration of the replacement material form anulus fibrosus and the resulting damage.

The replacement material according to the present invention has a shape having a hollow region that is comfortably fitted to the prosthetic space (hereinafter, referred to simply as shape having a hollow region), when it absorbs water or when it is placed in the hydrated state. Typical examples of the shape having a hollow region include cylindrical shapes such as almost cylindrical, almost elliptically cylindrical and almost polygonally cylindrical; hollow three-dimensional shapes such as hollow spherical, almost semi-spherical, almost cylindrical rod, and almost prism; and the like. For effective reduction in size of the replacement material in the dehydrated state, the shape of the replacement material according to the present invention in the hydrated state is preferably cylindrical, in particular almost cylindrical or almost elliptically cylindrical.

Figure 2:
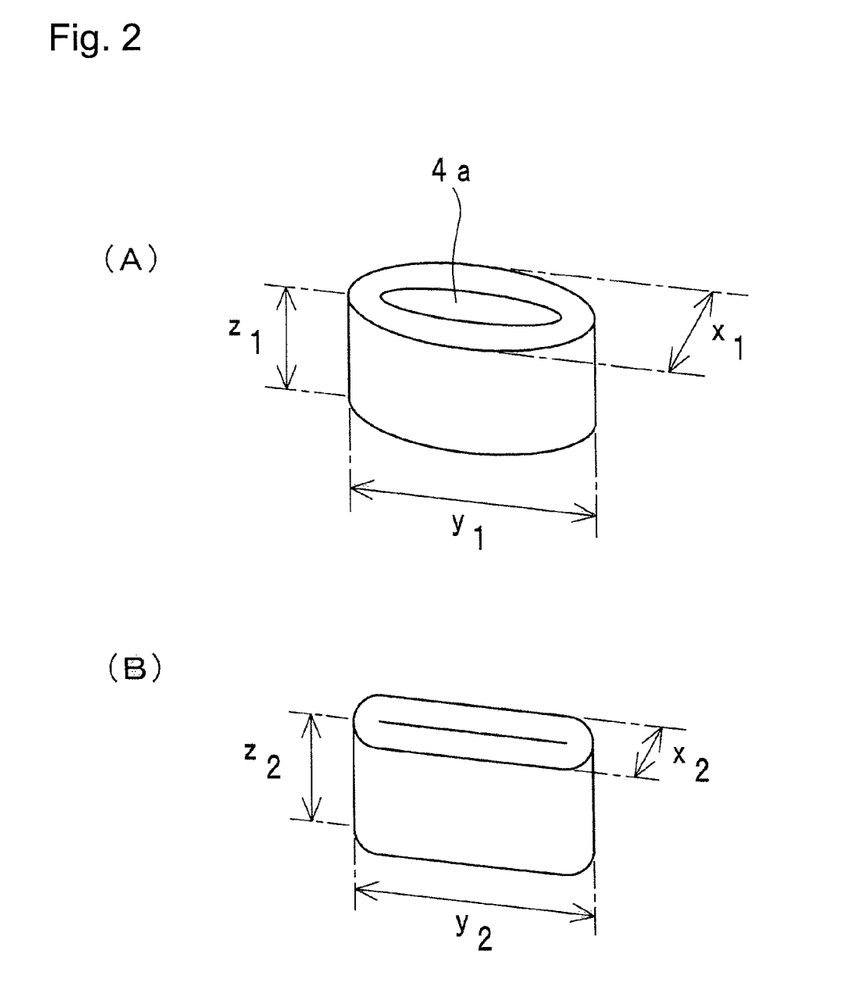
FIG. 2(A) is a schematic sketch drawing illustrating the shape of a PVA hydrogel test specimen after immersion in physiological saline in an Example.
FIG. 2(B) is a schematic sketch drawing illustrating the shape of a test specimen of dry PVA gel before immersion in physiological saline in an Example.

For example, the elliptically cylindrical shape is the shape shown in FIG. 2(A), wherein 4a in the Figure represents the hollow region.

The dimension of the shape of the replacement material according to the present invention in the hydrated state is so adjusted properly according to the size of the intervertebral disk and the prosthetic space to be inserted that it fits to the prosthetic space to be inserted. When the replacement material is placed inside the prosthetic space in the hydrated state (saturated), the outermost surface of the replacement material may not fit to the internal surface of the prosthetic space strictly as far as the object of the present invention is achieved.

Specifically, there may be a gap between the side wall of the replacement material and the anulus fibrosus.

Specifically as for the size of the shape in the hydrated state, when the replacement material is almost elliptically cylindrical as shown in FIG. 2(A), the minor axis $x_1$ and the major axis $y_1$ of the cross section in the direction vertical to the length direction are respectively 10 to 15 mm and 10 to 30 mm, and the height (thickness) $z_1$ is 5 to 20 mm. In particular, the height $z_1$ is preferably made longer by approximately 1 to 5 mm than the height of the prosthetic space. The side wall of the replacement material in such an almost elliptical cylindrical shape has a thickness normally of 4 to 15 mm. The thickness is the value of the PVA material itself for replacement material. The thickness may not be uniform and may vary in the range above.

Figure 3:
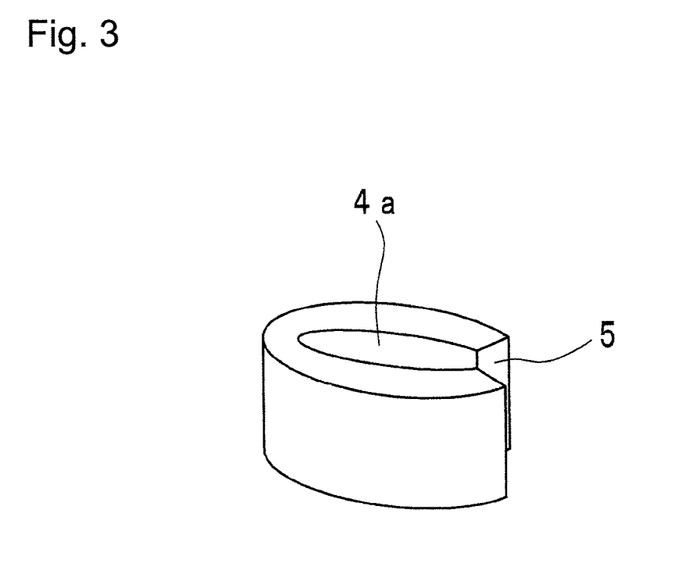
FIG. 3 is a schematic sketch drawing illustrating an example of the shape that the spinal intervertebral disk replacement material according to the present invention may have after water absorption.

The cylindrical shape and the hollow 3D shape may have a side wall not completely uniform, and thus, may have a slit stretching from the top to the bottom in part of the side wall. It is because the replacement material according to the invention has an excellent load-supporting property and exhibits a sufficient load-supporting property even with such a slit. An example of the cylindrical shape with such a slit is the shape shown in FIG. 3. In FIG. 3, 5 represents the slit.

The replacement material according to the present invention in the dehydrated state before water absorption has a shape wherein the replacement material is so deformed that there is no hollow region, for example by flattening, or the internal face of the hollow region is in contact with itself. Typical examples of the shapes include flat almost elliptical columnar shape, flat almost circular columnar shape, and the like. An example of the shape is the shape shown in FIG. 2(B). By adopting a shape of the replacement material according to the present invention wherein the hollow region disappears in the dehydrated state, it is possible to insert the replacement material through a relatively small incision opening for insertion into the prosthetic space and to avoid the damage of anulus fibrosus during operation.

The shape of the replacement material according to the present invention in the dehydrated state before water absorption is not limited, if the shape and the size thereof in the hydrated state are fitted to the prosthetic space. For example when the replacement material has a flat almost elliptical columnar shape in which the hollow region is flattened and the internal face is in contact with itself, as shown in FIG. 2(B), normally, the entire thickness $x_2$ is 2 to 10 mm; the entire length $y_2$ is 10 to 30 mm; and the entire height $z_2$ is 3 to 18 mm. In FIG. 2(B), the replacement material is shown flat or planar in the dehydrated state, but the shape may be curved.

For prevention of drop or separation out of the anulus fibrosus and also for prevention of induction of hernia symptoms by excessive swelling, the replacement material according to the present invention preferably has a volume swelling ratio of 135 vol % or less, more preferably 110 to 120 vol %.

The volume swelling ratio is the ratio of the volume in the dehydrated state to the volume in the hydrated state (hydration state/dehydration state). A volume in any condition is the volume of the replacement material itself, and is determined according to the Archimedes method similarly to the shape deformation rate above.

The replacement material according to the present invention changes its shape and reclaims its predetermined shape within 24 hours, preferably 12 hours, more preferably 3 hours, after insertion into the anulus fibrosus in the body. Specifically, the shape change occurs after insertion before the patient begins to move after operation, preferably before completion of the operation.

Because the replacement material according to the present invention has a shape in which the hollow region disappears during insertion into the prosthetic space and thus a gap derived from the hollow region, it is possible to place cells or cells and a biodegradable substrate in the gap. Presence of these substances, which accelerates cure of the anulus fibrosus structure and the surrounding structure, is effective in preventing undesirable separation of the replacement material.

In addition, a mucopolysaccharide such as sodium hyaluronate may be coated on the top and bottom sliding faces of the replacement material according to the present invention. Such a substance has a very high water-holding property and makes the replacement material exhibit a favorable sliding property, as it is functioning as an assistant for cartilage sliding movement and forming an elastic-fluid lubrication state or an interfacial lubrication state according to its concentration.

(Method of Preparing Spinal Intervertebral Disk Replacement Material)

The method of producing a spinal intervertebral disk replacement material according to the present invention is characterized by providing the replacement material with an ability of shape memory by γ-ray irradiation of the PVA hydrogel having a particular percentage of saturated water content.

Specifically, a PVA gel having a percentage of saturated water content of 20 to 53 wt %, preferably 25 to 37 wt %, is first prepared (step A). The PVA gel obtained may be in the dehydrated state or in the hydrated state, in particular in the saturated hydration state. The preparing method is not particularly limited, and any one of the methods commonly used conventionally in the field of PVA hydrogel may be used. For example, a PVA solution is obtained by adding and dissolving PVA in a mixed solution of dimethylsulfoxide (DMSO) and water, and the PVA solution is gelated at a low temperature of about −20 to −10° C.

Then, the PVA gel is washed with ethanol, replacing the solvent with ethanol, and heat-treated under reduced pressure at 60 to 140° C., to give a dry PVA gel having the above percentage of saturated water content in the dehydrated state. Subsequent immersion of the dry PVA gel in nitrogen-substituted water gives a PVA hydrogel in the hydrated state. Sufficiently hydrogelation by immersion for 48 hours or more in particular gives a PVA hydrogel in the saturated hydration state.

The percentage of saturated water content can be controlled by adjustment of the vacuum heat-treatment temperature, vacuum heat-treatment period, and others. For example, increase in vacuum heat-treatment temperature results in decrease of the percentage of saturated water content. Alternatively, decrease of the vacuum heat-treatment temperature leads to increase of the percentage of saturated water content. Alternatively, extension of the vacuum heat-treated period, for example, leads to decrease of the percentage of saturated water content. Yet alternatively, shortened vacuum heat-treated period leads to increase of the percentage of saturated water content.

The PVA according to the present invention used is not particularly limited, if the object of the present invention is achieved, but preferably has a polymerization degree, for example, of 5,000 to 10,000.

Then, the PVA gel obtained in step A is converted to a PVA hydrogel in the shape having a hollow region described above in the hydrated state (step B). The PVA hydrogel, if obtained in the previous step, may be cut and shaped as it is. The shape formed in the step is memorized and restored in the prosthetic space.

The forming method is not particularly limited, if a desirable shape is formed, but, for example, a method of forming a desirable shape in a mold or the like is employed.

After formed, the PVA hydrogel is irradiated with γ ray at an intensity of 20 to 100 kGy, preferably 50 to 100 kGy (step C). Irradiation of γ ray in a suitable quantity provides the replacement material according to the present invention with an ability of shape memory. Namely, it causes crosslinking of the PVA molecular chains, without sacrifice of mechanical properties and percentage of saturated water content inherent to the PVA hydrogel. The crosslinking generates crosslinking points in the PVA molecular chains, making the resin function as so-called spring and change into (reclaim) a particular shape in the course from the deformed and dry state (dehydration state) to the hydrated state. The ability of shape memory allows repeated reversion to the particular shape. A limited amount of γ-ray irradiation results only in cleavage mainly of the PVA main chain but not to recombination and crosslinking of the main chains, consequently making it difficult to reclaim the shape after water absorption and leading to insufficient ability of shape memory and possibly to insufficient shape deformation. An excessive quantity of γ-ray irradiation leads to sufficient load resistance and ability of shape memory of the PVA hydrogel, but the replacement material may damage the vertebral body endplate cartilage and the anulus fibrosus in contact therewith because of its high rigidity.

The γ-ray irradiation is preferably performed in water substituted with nitrogen at a low-oxygen concentration. It is because the dissolved oxygen present in water first causes cleavage of the PVA molecular chain, leading to oxidative degradation of the PVA hydrogel and deterioration in the ability of shape memory and other mechanical properties.

The amount of the γ-ray irradiation may be determined by using a film dosemeter, a polymethyl methacrylate dosemeter, or a calorimeter. During γ-ray irradiation, the PVA hydrogel is normally placed in a sealed container together with nitrogen-substituted physiological saline, and the dosemeter is placed in the region close to the sealed container for measurement.

After γ-ray irradiation, the PVA hydrogel in the shape having a hollow region is dried in the state where it is deformed in such a manner that the hollow region disappears, for example in such a manner that the hollow region is flattened under pressure, to give a replacement material according to the present invention of the dry PVA gel (step D). The drying condition is not particularly limited, if the dry PVA gel obtained in the dehydrated state can have its hollow region-disappeared shape without external force, and normally, the replacement material is left and dried under such conditions at room temperature for 48 hours or more.

The forming step B may be performed simultaneously with step A. Specifically, for example in step A, the PVA solution may be gelated in a mold for giving a desirable shape while it is gelated at a low temperature.

Alternatively, the forming step B may be performed between the γ-ray irradiation step C and the drying step D. Specifically, a PVA hydrogel is prepared (step A), the PVA hydrogel is irradiated with γ ray (step C), and then, the PVA hydrogel is formed into the shape having a hollow region. It is then dried in the state where the replacement material is deformed in such a manner that the hollow region disappears, to give a replacement material of dry PVA gel according to the present invention (step D).

It is possible to control the shape deformation rate and the volume swelling ratio of the replacement material according to the present invention, by adjusting the size of the hollow region in the shape obtained after formed, the vacuum heat-treatment temperature, and the vacuum heat-treatment period in the production method for the replacement material described above.

For example, enlargement of the hollow region in the shape formed after molding results in increase of the shape deformation rate. Alternatively, shrinkage of the hollow region leads to decrease in the shape deformation rate. For example, increase in vacuum heat-treatment temperature leads to decrease in the volume swelling ratio.

Alternatively, decrease in the vacuum heat-treatment temperature leads to increase of the volume swelling ratio. For example, elongation of the vacuum heat-treated period leads to decrease of the volume swelling ratio.

Alternatively, shortening of the vacuum heat-treated period leads to increase of the volume swelling ratio.

EXAMPLES

Hereinafter, the invention will be described specifically with reference to Examples and drawings, but it should be understood that the invention is not limited thereby.

Example 1

PVA (polymerization degree: 8800) (10 wt parts) was added to a mixture (90 wt parts) of dimethylsulfoxide (DMSO) and water at a weight ratio of 80:20, and the mixture was dissolved at 120 to 140° C., to give a PVA solution. The PVA solution was poured into a form giving a formed product in the hollow disk shape shown in FIG. 2(A), and then, the mold was rapidly cooled at −15° C. After rapid cooling, the PVA gel was removed from the mold and washed with ethanol for replacing DMSO and water with ethanol in the PVA gel. The PVA gel was then subjected to a vacuum heat treatment under a reduced pressure of 1 Torr at 140° C. for 3 hours. The PVA gel was immersed in nitrogen-substituted water for 48 hours or more for hydrogelation. The percentage of saturated water content of the PVA hydrogel was 35 wt %. The PVA hydrogel with the shape shown in FIG. 2(A) was obtained by γ-ray irradiation to the PVA hydrogel in nitrogen-substituted water of low oxygen concentration at an irradiation intensity of 0, 25, 50, 75, 100, or 125 kGy. After γ-ray irradiation, the PVA hydrogel was sufficiently dried at room temperature, while the deformation with flattened hollow region 4a is preserved, to give a test specimen of dry PVA gel in the shape shown in FIG. 2(B).

The obtained test specimen of dry PVA gel was immersed in physiological saline at 37° C., and shape recovery of the test specimen was observed. The size of the test specimen before immersion, the size of the test specimen and the percentage of saturated water content after shape recovery, the volume swelling ratio, and the shape deformation rate were measured, and the ability of shape memory was evaluated. The results are summarized in Table 1.

The size of the test specimen before immersion is the size of the test specimen before immersion in physiological saline: $x_2$, $y_2$, and $z_2$ in FIG. 2(B).

The size of the test specimen after shape recovery is the size of the test specimen including the hollow region after immersion in physiological saline for 48 hours: $x_1$, $y_1$, and $z_1$ in FIG. 2(A). The thickness of any test specimen was at least 4 mm and at most 5 mm.

The ability of shape memory was evaluated according to the following criteria: In the present invention, the rank ○ or higher is the range practically without problem, and the rank ◎ is preferable.

◎: Recovery to the shape in FIG. 2(A) within 12 hours after immersion in physiological saline;
○: Recovery to the shape in FIG. 2(A) within 24 hours after immersion in physiological saline;
Δ: Recovery to the shape in FIG. 2(A) within 36 hours after immersion in physiological saline;
X: Recovery to the shape in FIG. 2(A) within 48 hours after immersion in physiological saline;
XX: No recovery to the shape in FIG. 2(A) even after 48 hours after immersion in physiological saline.

In particular, the dry PVA gel obtained in condition A3 reclaimed a hollow disk in the shape shown in FIG. 2(A) after immersion in physiological saline in 30 minutes. The reclaimed shape remained constant even if the immersion period is elongated, and no excessive swelling was observed.

TABLE 1

| | γ-Ray irradiation amount (kGy) | Test specimen size before soaking ($x_2 \times y_2 \times z_2$) (mm) | Test specimen size after shape recovery ($x_1 \times y_1 \times z_1$) (mm) | Percentage of saturated water content after shape recovery (wt %) | Volume swelling ratio (vol %) | Shape deformation rate (vol %) | Ability of shape memory |
|---|---|---|---|---|---|---|---|
| Condition A1 | 0 | 8 × 25 × 9 | 9 × 28 × 10 | 35.3 | 113 | 140 | XX |
| Condition A2 | 25 | 8 × 25 × 9 | 12 × 25 × 10 | 34.7 | 113 | 167 | ○ |
| Condition A3 | 50 | 8 × 25 × 9 | 15 × 25 × 10 | 34.2 | 114 | 208 | ◉ |
| Condition A4 | 75 | 8 × 25 × 9 | 15 × 25 × 10 | 33.7 | 114 | 208 | ◉ |
| Condition A5 | 100 | 8 × 25 × 9 | 15 × 25 × 10 | 33.2 | 114 | 208 | ◉ |

As apparent from Table 1, the shape recovery was slow in the case of no γ-ray irradiation, but the shape recovery was fast in the case of γ-ray irradiation, i.e. the γ-ray irradiation of 25 kGy or more recovered the shape in 24 hours, particularly the irradiation of 50 kGy or more recovered the shape in 12 hours.

Example 2

PVA (polymerization degree: 8800) (10 wt parts) was added to a mixture (90 wt parts) of dimethylsulfoxide (DMSO) and water at a weight ratio of 80:20, and the mixture was dissolved at 120 to 140° C., to give a PVA solution. The PVA solution was rapidly cooled at −15° C. Then, the PVA gel was washed with ethanol, replacing DMSO and water with ethanol in the PVA gel, and the resulting gel was subjected to a vacuum heat treatment under a reduced pressure of 1 Torr at 60 to 140° C. The PVA gel was soaked in nitrogen-substituted water for 48 hours or more for hydrogelation.

In this way, PVA hydrogels having a percentage of saturated water content of 20, 25, 30, 35, 50 and 60 wt % were prepared. PVA hydrogel having a percentage of saturated water content of 15 wt % was prepared only unsuccessfully, because of low reactivity in thermal condensation polymerization, and it was difficult to prepare a hydrogel with a desired water content. The PVA hydrogel obtained was molded into a cylindrical shape having an external diameter 22 mm, an internal diameter 10 mm, and a thickness 3 mm. A test specimen of PVA hydrogel was obtained by γ-ray irradiation to the molded PVA hydrogel in nitrogen-substituted water at a low oxygen concentration.

A load was applied onto each PVA hydrogel test specimen at a load speed of 0.5 mm/min in a compression testing machine manufactured by Aikoh Engineering Co., Ltd. The compression properties observed in the compression test are summarized in Table 2, together with the condition for preparation of the PVA hydrogel. For comparison, a biological test specimen having a major axis diameter of 24 mm, a minor axis diameter of 16 mm, and a thickness of 3 mm was collected from canine lumbar vertebrae and used for evaluation.

After γ-ray irradiation, the PVA hydrogel test specimen was dried sufficiently with its hollow region flattened at room temperature, to give a test specimen of dry PVA gel in the shape shown in FIG. 2(B). The test specimen of dry PVA gel obtained was immersed in physiological saline at 37° C., and the shape recovery was examined. The percentage of saturated water content, the volume swelling ratio and the shape deformation rate after shape recovery were determined, and the ability of shape memory was evaluated. Results are summarized in Table 2. The ability of shape memory was evaluated in a similar manner to that in Example 1, except that "the shape shown in FIG. 2(A)" is replaced with "cylindrical shape". In the present invention, the rank ○ or higher is the range practically without problem, and the rank ◉ is preferable.

TABLE 2

| | Vacuum heat-treatment temperature (° C.) | Vacuum heat-treatment period (hr) | γ-Ray irradiation amount (kGy) | Percentage of saturated water content before γ-ray irradiation (%) | Percentage of saturated water content after shape recovery (%) | Compression rigidity (N/mm) | Compression Young's modulus (MPa) | Volume swelling ratio (vol %) | Shape deformation rate (vol %) | Ability of shape memory |
|---|---|---|---|---|---|---|---|---|---|---|
| Condition B1 | — | — | — | 15 | — | No test specimen prepared | No test specimen prepared | — | — | — |
| Condition B2 | 140 | 12 | 50 | 20.1 | 19.5 | 2231.7 | 21.3 | 110 | 209 | ◉ |
| Condition B3 | 140 | 6 | 50 | 25.4 | 24.7 | 1994.2 | 19.0 | 111 | 208 | ◉ |
| Condition B4 | 140 | 4 | 50 | 30.4 | 29.8 | 1633.3 | 15.6 | 111 | 208 | ◉ |
| Condition B5 | 140 | 3 | 50 | 35.2 | 34.7 | 942.5 | 9.0 | 113 | 208 | ◉ |
| Condition B6 | 60 | 48 | 50 | 50.0 | 49.9 | 624.8 | 6.3 | 132 | 215 | ◉ |
| Condition B7 | 60 | 6 | 50 | 60.2 | 60.0 | 480.2 | 4.6 | 144 | 219 | ◉ |
| Comparison | — | — | — | — | — | 565.3 | 5.6 | — | — | — |

—: Not measured

As apparent from Table 2, it was not possible to prepare a hydrogel having a water content of 15 wt % before γ-ray irradiation under the condition B1, as described above. The hydrogel having a water content of 60.2 wt % before γ-ray irradiation obtained under the condition B7 had an ability of shape memory, but was lower in rigidity than that of the comparative biological test specimen, and it was difficult to obtain a test specimen with favorable load resistance. In contrast, any one of the hydrogels having a water content of 20.1 wt %, 25.4 wt %, 30.4 wt %, 35.2 wt %, and 50 wt % before γ-ray irradiation was higher in rigidity than that of the comparative biological test specimen, and it was possible to obtain a test specimen with favorable load resistance. In particular, the hydrogel at 25 wt %, 30 wt %, or 35 wt % gave a test specimen having a compression rigidity sufficient for preserving the vertebral body.

INDUSTRIAL APPLICABILITY

The spinal intervertebral disk replacement material for nucleus pulposus according to the invention and the production method thereof are useful in the fields of orthopedics and neurosurgery, in particular for treatment of the intervertebral disk damaged, for example, by disease such as hernia of intervertebral disk or by accident.

The invention claimed is:

1. A method for replacing a nucleus pulposus in an intervertebral disk, which method comprises:
   providing a spinal intervertebral disk replacement molded-dry-product for nucleus pulposus which has a hollow region disappeared comprising a polyvinylalcohol gel that is irradiated with γ ray at an intensity of 50 to 100 kGy; and
   inserting the spinal intervertebral disk replacement molded-dry-product for nucleus pulposus into a prosthetic space inside an anulus fibrosus through an incision opening of the anulus fibrosus,
   wherein the molded-dry-product changes its shape into an almost cylindrical or almost elliptically cylindrical shape so that a hollow region comes into existence at a shape deformation rate of 200 vol % or more and at a volume swelling ratio of 135 vol % or less by water absorption,
   wherein the percentage of saturated water content of said polyvinylalcohol gel before irradiation is 18 to 25 wt %.

2. The method of claim 1, wherein the molded-dry-product has a colunmar shape in which a sectional view is almost elliptical and an internal face is in contact with itself.

3. The method of claim 1, wherein the γ-ray irradiation dose is 50 to 100 kGy.

* * * * *